United States Patent [19]

Naik et al.

[11] Patent Number: 5,225,413

[45] Date of Patent: Jul. 6, 1993

[54] PH-NEUTRAL AQUEOUS SOLUTIONS OF QUINOLONE-CARBOXYLIC ACIDS

[75] Inventors: Arundev H. Naik; Herbert Voege, both of Leverkusen, Fed. Rep. of Germany

[73] Assignee: Bayer-Aktiengesellschaft, Leverkusen, Fed. Rep. of Germany

[21] Appl. No.: 620,435

[22] Filed: Nov. 30, 1990

Related U.S. Application Data

[63] Continuation of Ser. No. 406,207, Sep. 12, 1989, abandoned.

[30] Foreign Application Priority Data

Sep. 16, 1988 [DE] Fed. Rep. of Germany ....... 3831514

[51] Int. Cl.$^5$ ..................... A01N 43/60; C07D 401/04
[52] U.S. Cl. ................... 514/254; 514/235.2; 514/312; 544/128; 544/363; 546/156
[58] Field of Search ............... 544/363, 128; 546/156; 514/235.2, 254, 312

[56] References Cited

U.S. PATENT DOCUMENTS

| | | | |
|---|---|---|---|
| 4,772,605 | 9/1988 | Naik et al. | 544/363 |
| 4,792,552 | 12/1988 | Simonovitch | 544/363 |
| 4,808,583 | 2/1989 | Grohe et al. | 514/254 |

OTHER PUBLICATIONS

N. B. Behrens et al., "Metal Complexes of the Antibiotic Nalidixic Acid", Inorganica Chimica Acta, V. 125, 1986, pp. 21–26.
C. H. Spurlock, "Increasing solubility of Enoxacin and Norfloxacin by Means of Salt Formation", J. of Parental Science & Techn., V. 40, 1986, pp. 70–72.

*Primary Examiner*—Thurman K. Page
*Assistant Examiner*—Jyothsna Venkat

[57] ABSTRACT

A pH-neutral aqueous solution of a quinolonecarboxylic acid of the formula

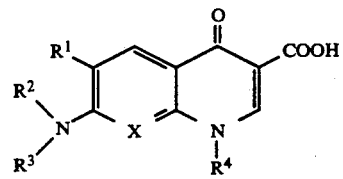

in which
$R^1$ represents halogen, $C_{1-4}$-alkyl or $C_{2-4}$-alkenyl,
$R^2$ and $R^3$ represent hydrogen, $C_{1-4}$-alkyl, or together the adjacent nitrogen atom form an optionally substituted morpholine or piperazine ring,
$R^4$ represents optionally substituted $C_{1-4}$-alkyl or $C_{3-6}$-cycloalkyl,
X represents —N= or —$CR^5$=, and
$R^5$ represents hydrogen, halogen, OH or $C_{1-4}$-alkyl, or
$R^4$ and $R^5$, together with the C and N atoms positioned between them, form a saturated 5- or 6-membered ring which can contain other hetero atoms and which is optionally substituted, the solution containing calcium ions in at least an equimolar amount relative to the quinolonecarboxylic acid and having a pH between about 6.5 and 7.5. The solution is prepared by reacting the quinolonecarboxylic acid in water with a water-soluble calcium compound in at least an equimolar ratio and subsequently adjusting the pH of the solution to a value between about 6.5 and 7.5. The solutions are especially suited for treating eggs and drinking water.

8 Claims, No Drawings

PH-NEUTRAL AQUEOUS SOLUTIONS OF QUINOLONE-CARBOXYLIC ACIDS

This application is a continuation of application Ser. No. 406,207, filed Sep. 12, 1989, now abandoned.

The present invention relates to pH-neutral aqueous solutions of quinolonecarboxylic acids, their preparation and their use as bactericides.

Eggs for hatching are treated with bactericides in order to prevent losses by bacterial infections. For this purpose, the solution of a bactericide is injected into the eggs, for example by means of a syringe. The method has the advantage that each egg receives a defined amount of active compound. However, the method is labor-intensive.

It is simpler to treat the eggs by dipping. In order to facilitate penetration of the active compound through the protective layer of the eggs, the eggs are either initially warmed (the air bubble in the egg expands) and then dipped into a cold active compound solution, or the eggs are dipped into an active compound solution, and the latter, together with the eggs, are placed in a vacuum. In both methods, a small amount of active compound solution is sucked through the egg shell. However, the amount of active substance which is taken up varies widely, depending on the constitution of the shell.

Such treatments of eggs for hatching with bactericides and antibiotics, such as, for example, gentamycin, tetracyclineand chloramphenicol were already known. The effect of these active compounds, in particular against resistant strains of bacteria and against mycoplasma, were not fully satisfactory in practice. Therefore, it was desirable to treat eggs for hatching with active compounds of the type of the quinolonecarboxylic acids.

Quinolonecarboxylic acids are only sparingly soluble in neutral water. Due to their betaine character, they can be dissolved in acid or alkaline aqueous solutions by salt formation. However, such solutions are very sensitive against variations in the pH- range.

Acid solutions cannot be employed for the treatment of eggs since they attack the egg shell too severely. Alkaline solutions are, in principle, suitable for the treatment of eggs, but have the disadvantage that they dissolve small amounts of magnesium and calcium ions out of the egg shell (no damage to the egg). Due to the very poor solubility of the magnesium salt of the quinolonecarboxylic acids, a precipitate is formed in the treatment solution. As more eggs are treated, more of the active compound is depleted. It is then necessary to replace not only the solution which has been used up but also to add the active compound, which has fallen out of solution, in order to maintain the concentration of the dissolved active compound in the treatment solution (Replenishment).

Similar problems can occur wherever aqueous solutions of quinolonecarboxylic acids are employed. It was therefore desirable that pH-neutral, stable aqueous solutions of quinolonecarboxylic acids be provided in which the active compound does not precipitate in the form of sparingly-soluble salts.

The invention relates to pH-neutral aqueous solutions of quinolonecarboxylic acids, which are obtained when quinolonecarboxylic acids are treated with water-soluble calcium salts in at least an equimolar ratio, and the pH- of the solution is subsequently adjusted to a value of between 6.5 and 7.5.

The invention furthermore relates to a process for the preparation of pH-neutral aqueous solutions of quinolonecarboxylic acids, which is characterized in that quinolonecarboxylic acids are reacted in water with water-soluble calcium salts in at least an equimolar ratio, and the pH of the solution is subsequently adjusted to a value of between 6.5 and 7.5.

The invention furthermore relates to the use of the prepared solutions, for example for the treatment of eggs, as drinking water formulations, infusions, and in all those cases where pH-neutral aqueous solutions of quinolonecarboxylic acids are required.

It was surprising that in this manner stable, pH-neutral aqueous solutions of quinolonecarboxylic acids may be prepared. On the one hand, the magnesium salts of quinolonecarboxylic acids are very sparingly soluble in water. On the other hand, quinolonecarboxylic acids also form sparingly soluble salts with stoichiometric amounts of calcium salt. It is only with equimolar amounts of calcium salt and quinolonecarboxylic acid that a stable aqueous solution is obtained.

Suitable quinolonecarboxylic acids are the quinolonecarboxylic acids of the general formula I

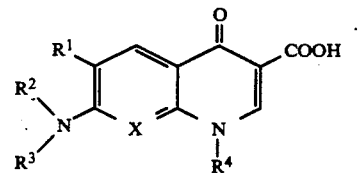

in which $R^1$ represents halogen, $C_{1-4}$-alkyl or $C_{2-4}$-alkenyl, $R^2$ and $R^3$ represent hydrogen, $C_{1-4}$-alkyl, or together with the adjacent nitrogen atom form an optionally substituted morpholine or piperazine ring. Substituents which may be present are $C_{1-4}$-alkyl and $C_{1-4}$-hydroxyalkyl.

$R^4$ represents $C_{1-4}$-alkyl or $C_{3-6}$-cycloalkyl, each of which is optionally substituted.

X represents —N= or —CR$^5$=, and $R^5$ represents hydrogen, halogen, OH or $C_{1-4}$-alkyl, or $R^4$ and $R^5$, together with the C and N atoms positioned between them, can form a 5- or 6-membered ring which can contain other hetero atoms and which is optionally substituted.

Compounds of the formula I which are preferably used are those in which $R^1$ represents fluorine, chlorine or bromine, $R^2$ and $R^3$ together with the adjacent nitrogen atom form a morpholine or piperazine ring, each of which is optionally substituted by $C_{1-4}$-alkyl or $C_{1-4}$-hydroxyalkyl, $R^4$ represents $C_{1-4}$-alkyl or cyclopropyl, X represents —N= or —CR$^5$=, and $R^5$ represents hydrogen, fluorine, chlorine or bromine, or $R^4$ and $R^5$, together with the atoms positioned between them, can form a saturated 6-membered ring which optionally contains O as a further hetero atom and which is optionally substituted by $C_{1-4}$-alkyl.

Compounds of the formula I which are particularly preferably used are those in which $R^1$ represents fluorine, $R^2$ and $R^3$ together with the adjacent nitrogen atom form a piperazine ring which is optionally substituted by $C_{1-4}$-alkyl or $C_{1-4}$-hydroxyalkyl, $R^4$ represents ethyl or cyclopropyl, X represents N= or =CR$^5$=, and $R^5$ represents hydrogen or fluorine, or $R^4$ and $R^5$, together with the atoms positioned between them, can form a saturated 6-membered ring which is optionally substituted by methyl or ethyl.

The following may be mentioned in particular: 1-Cyclopropyl-6-fluoro-1,4-dihydro-4-oxo-7-(1-piperazinyl-)quinoline-3-carboxylic acid (ciprofloxacin), 1-Cyclopropyl-6-fluoro-1,4-dihydro-4-oxo-7-(4-ethyl-1-piperazinyl-)quinoline-3-carboxylic acid (enrofloxacin), 1-Ethyl-6-fluoro-1,4-dihydro-4-oxo-7-(1-piperazinyl)-quinoline-3-carboxylic acid, 1-Ethyl-6-fluoro-1,4-dihydro-4-oxo-7-(1-piperazinyl)-1,8-naphthydrine-3-carboxylic acid, and 9-Fluoro-3-methyl-10-(4-methyl-1-piperazinyl)-7-oxo-2,3-dihydro-7,4-pyrido[1,2,3-de]1,4-benzoxazine-6-carboxylic acid.

Water-soluble calcium salts which are suitable are: calcium acetate, calcium chloride, calcium bromide, calcium nitrate, calcium phosphates and the hydrates thereof. Calcium chloride and the hydrates thereof may be mentioned in particular.

The calcium salts can also be formed using calcium hy-droxide or calcium oxide.

Water is used as the solvent for the preparations according to the invention. If appropriate, it is also possible to use mixtures of water with other solvents. The solvents include: alcohols, such as monohydric or polyhydric primary, secondary or tertiary alkanols, such as, for example, ethanol, butanol, benzyl alcohol, glycol, glycerol, propylene glycol, and also N-methylpyrrolidone.

The concentration of the solvents employed in the preparations according to the invention, in addition to water, is 1 to 30%, preferably between 1 to 10%, very particularly preferably between 1 to 3%.

Customary additives can be added to the preparations according to the invention. Non-toxic pharmaceutical substances, such as diluents, absorption accelerators, absorption inhibitors, substances which delay crystallization, sequestering agents, antioxidants, preservatives, and protonization agents come as such. The following may be mentioned particularly preferably: preservatives, such as, for example, p-hydroxy-benzoic acid esters, benzyl alcohol or phenols, antioxidants, such as, for example, sodium meta-bisulphite or sodium sulphite, sequestering agents, such as sodium salts of ethylenediaminetetraacetic acid, and substances which delay crystallization, such as polyvinyl pyrrolidone.

The concentration of the auxiliaries in the preparations according to the invention is 0.1 to 10%, preferably 1 to 2%.

The compounds of the formula I lie in the preparations according to the invention in concentrations of 0.1 to 30%, preferably 0.5 to 10% or 0.2 to 2% or 10 to 30%, depending on the type of application. Solutions containing 0.5 to 10% of compound of the formula I are particularly preferred. For this purpose, the calcium salts are employed in 1- to 5-fold the equimolar amount, preferably in approximately equimolar amount.

The pH of the preparations according to the invention is between 6.5 and 7.5, preferably 7.

In order to prepare the preparations according to the invention, the compounds of the formula I can be dissolved in water, and the required amount of calcium salt as such or in the form of its aqueous solution can be incorporated in this solution. The solution obtained is subsequently neutralized with acid. In this manner, ready-for-use solutions of the active substance, packaged in suitable containers, for example in ampoules, injection, bottles or infusion bottles, and also those unfinished products which are suitable for solutions, for example concentrates, can be prepared.

The solutions according to the invention and also the compounds of the formula on which they are based are to be used as drugs for the control of bacterial infections. The solutions are particularly suitable for the treatment of eggs, for example against infections by bacteria or mycoplasms.

EXAMPLE 1

| 10% strength composition | |
|---|---|
| Enrofloxazin | 10.00 g |
| Potassium hydroxide, 85.3% strength | 1.80 g |
| Calcium chloride, 6H$_2$O | 27.30 g |
| 1N Hydrochloric acid to pH 7.0 | approx. 1.00 g |
| Benzyl alcohol | 1.00 g |
| Water | to 100.00 ml |

Potassium hydroxide was dissolved in water, the active compound enrofloxacin was subsequently added with stirring and dissolved, and calcium chloride was then stirred in. In this process, a precipitate formed. Hydrochloric acid was added with stirring until a clear solution of pH 7 was formed. The mixture was subsequently made up to 100 ml with water. Some of this solution was diluted with 99 parts of 5-fold WHO Standard Water, and no precipitates were observed over 25 days.

EXAMPLE 2

| | |
|---|---|
| 10% strength enrofloxacin solution in aqueous potassium hydroxide solution of pH 11 plus 1% of benzyl alcohol | 50 ml |
| 55% strength aqueous calcium chloride x 6 H$_2$O solution | 25 ml |
| 10% strength acetic acid solution | approx. 6.2–8.0 g |
| Water | to 100 ml |

Calcium chloride solution was added to the stirred enrofloxacin solution The precipitate which formed was dissolved by the addition of acetic acid while stirring was continued. The pH was controlled by the addition of acetic acid. Three formulations were prepared with the pH set to 6.7, 7.0 and 7.2, respectively.

Stability of the Formulations

The three formulations (pH 6.7, 7.0, 7.2) remained stable while stored for two months at 4° C. and 50° C.

Stability of the Dilution

The formulation (pH 7.0) was diluted 1:49 (=1000 ppm) in demineralized water, 20, 40, 60, 80 and 100 ppm of Mg$^{++}$ were added, and the mixture was observed over 26 days without precipitates being noticed.

It will be understood that the specification and examples are illustrative but not limitative of the present invention and that other embodiments within the spirit and scope of the invention will suggest themselves to those skilled in the art.

What is claimed is:

1. An aqueous solution of a quinolinecarboxylic acid of the formula

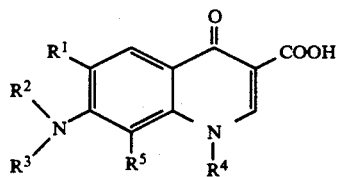

in which
R¹ represents halogen, $C_{1-4}$-alkyl or $C_{2-4}$-alkenyl,
R² and R³ represent hydrogen, $C_{1-4}$-alkyl, or together with the adjacent nitrogen atom form a morpholine or piperazine ring, each of which is optionally substituted by $C_{1-4}$-alkyl or $C_{1-4}$-hydroxyalkyl,
R⁴ represents optionally substituted $C_{1-4}$-alkyl or $C_{3-6}$-cycloalkyl, and
R⁵ represents hydrogen, halogen, OH or $C_{1-4}$-alkyl, the solution containing calcium ions in at least an equimolar amount relative to the quinolonecarboxylic acid and having a pH between about 6.5 and 7.5.

2. An aqueous solution according to claim 1, in which
R¹ represents fluorine, chlorine or bromine,
R² and R³ together with the adjacent nitrogen atom form a morpholine or piperazine ring, each of which is optionally substituted by $C_{1-4}$-alkyl or $C_{1-4}$-hydroxyalkyl,
R⁴ represents $C_{1-4}$-alkyl or cyclopropyl, and
R⁵ represents hydrogen, fluorine, chlorine or bromine.

3. An aqueous solution according to claim 1, in which
R¹ represents fluorine,
R² and R³ together with the adjacent nitrogen atom form a piperazine ring which is optionally substituted by $C_{1-4}$-alkyl or $C_{1-4}$-hydroxyalkyl,
R⁴ represents ethyl or cyclopropyl, and
R⁵ represents hydrogen or fluorine.

4. An aqueous solution according to claim 1, in which the quinolonecarboxylic acid is selected from the group consisting of 1-cyclopropyl-6-fluoro-1,4-dihydro-4-oxo-7-(1-piperazinyl-)quinoline-3-carboxylic acid, 1-cyclopropyl-6-fluoro-1,4-dihydro-4-oxo-7-(4-ethyl-1-piperazinyl-)quinoline-3-carboxylic acid, and 1-ethyl-6-fluoro-1,4-dihydro-4-oxo-7-(1-piperazinyl)quinoline-3-carboxylic acid.

5. An aqueous aqueous solution according to claim 1, wherein the quinolonecarboxylic acid is enrofloxacin.

6. An aqueous aqueous solution according to claim 5, containing 1 to 5 moles of water-soluble calcium salt per mole of enrofloxacin.

7. A process for the preparation of an aqueous aqueous solution of a quinolonecarboxylic acid according to claim 1, comprising reacting the quinolonecarboxylic acid in water with a water-soluble calcium compound in at least an equimolar ratio and subsequently adjusting the pH of the solution to a value between about 6.5 and 7.5.

8. In the protection of eggs and drinking water against bacterial infection by contact with a quinolonecarboxylic acid, the improvement wherein the quinolonecarboxylic acid is employed in the form of a solution according to claim 1.

* * * * *